United States Patent [19]

Heller

[11] Patent Number: 4,990,781

[45] Date of Patent: Feb. 5, 1991

[54] SPECTROSCOPICALLY OPERATING INFRARED HYGROMETER

[75] Inventor: Theodor Heller, Worthsee/Etterschlag, Fed. Rep. of Germany

[73] Assignee: Deutsche Forschungs-und Versuchsanstalt fur Luft-und Raumfahrt E.V., Cologne, Fed. Rep. of Germany

[21] Appl. No.: 276,603

[22] Filed: Nov. 28, 1988

[30] Foreign Application Priority Data

Nov. 27, 1987 [DE]  Fed. Rep. of Germany ....... 3740212

[51] Int. Cl.⁵ .................. G01N 25/56; G01J 5/06; G01J 5/08; G01J 5/62
[52] U.S. Cl. ........................ 250/347; 250/338.5; 250/339
[58] Field of Search ............ 250/343, 347, 339, 338.5, 250/338.1; 356/300, 326, 51, 436, 437, 438, 440

[56] References Cited

U.S. PATENT DOCUMENTS

| | | | |
|---|---|---|---|
| 3,364,351 | 1/1968 | Palmer | 250/338.5 |
| 4,083,249 | 3/1978 | Gerber | 374/20 |
| 4,526,034 | 7/1985 | Campbell | 250/504 R |

OTHER PUBLICATIONS

Hyson et al., "A Single-Beam Infrared Hygrometer for Evaporation Measurement", J. Appl. Met., 14, 1975, pp. 301–307.

Bogomolova et al., "Double-Beam Infrared Spectrometer for Measuring Humidity Fluctuations in the Atmosphere", Izv. Atm. and Oceanic Physics, vol. 10, 1974, pp. 933–942.

Buck, Arden L., "The Variable-Path Lyman-Alpha Hygrometer and Its Operating Characteristics", Bull. Amer. Met. Soc., vol. 57, No. 9, Sep. 1976, pp. 1113–1118.

Primary Examiner—Constantine Hannaher
Assistant Examiner—Edward J. Glick
Attorney, Agent, or Firm—Browdy and Neimark

[57] ABSTRACT

In a spectroscopically operating infrared hygrometer, beams emitted by the beam source and formed by the lens arrangement disposed in front thereof, are reflected via two pairs of rotating lenses, fixed in two parallel planes which are at a fixed distance from each other, and via a fixed mirror, to the lens arrangement placed in front of the detector and are directed by this lens arrangement to the detector. In this infrared hygrometer the absorption distance change takes place very rapidly, so that it is possible during measurements over longer perids of time, for example, during measurements taken from an airplane, to relate with small time constants the individual measurement values for the two absorption distances continuously. Furthermore, intermediate calibration is not required with this infrared hygrometer.

2 Claims, 1 Drawing Sheet

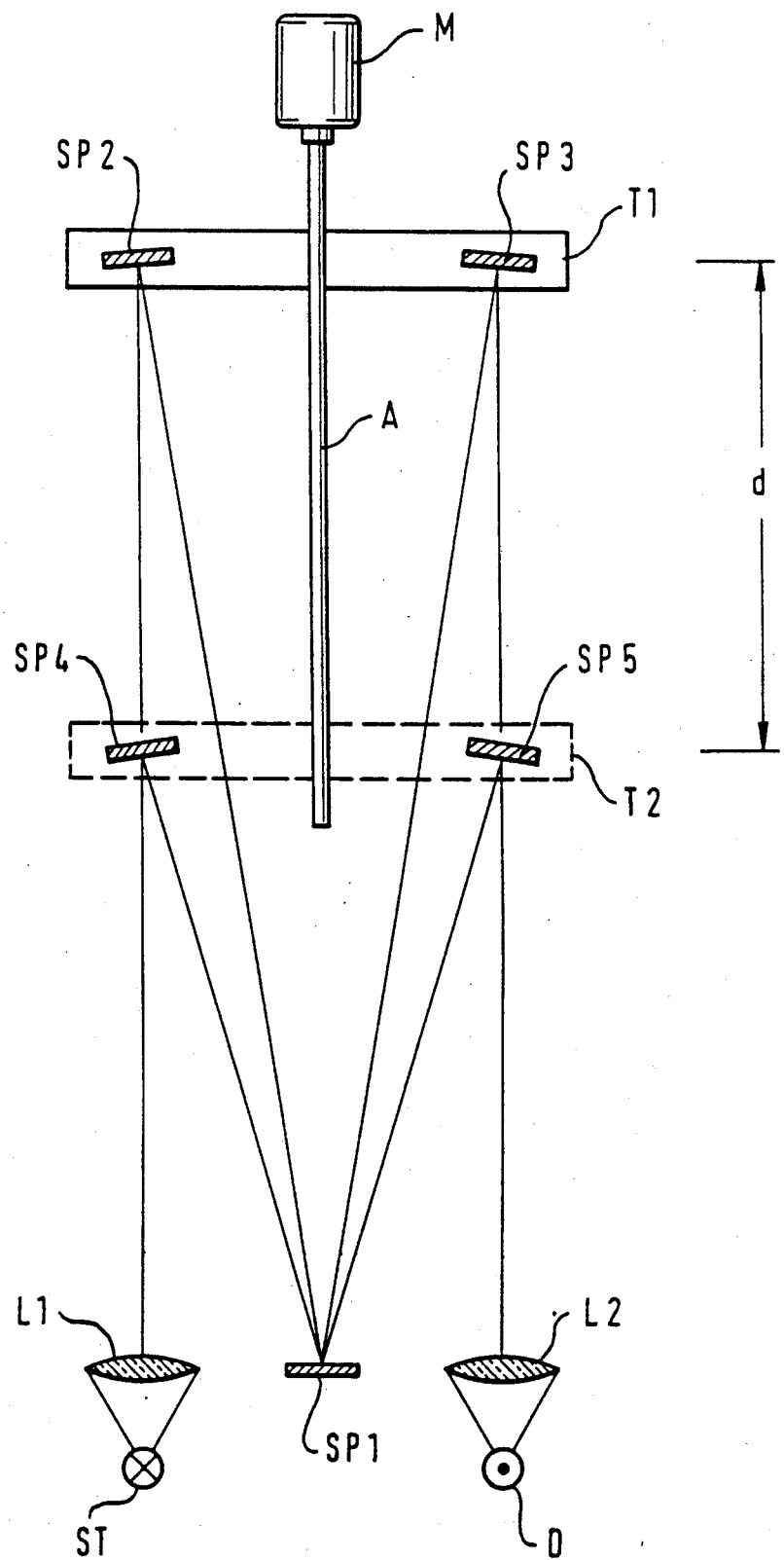

SPECTROSCOPICALLY OPERATING INFRARED HYGROMETER

FIELD OF THE INVENTION

The invention relates to a spectroscopically operating infrared hygrometer having a beam source and a detector, in front of each of which a lens arrangement is disposed for focusing and directing the beams.

BACKGROUND OF THE INVENTION

Devices for measuring the water vapor content of the atmosphere by means of spectroscopic methods have been known for a long time. The absorption spectrum of water vapor molecules extends across a very broad range of the spectrum. Devices are in use which operate at 1,215.6 Å, i.e. on the wave length of the so-called Lyman $\alpha$ line (these devices will be called L$\alpha$ devices hereinbelow). Furthermore, devices are known in which the absorption of water vapor in the infrared range of the spectrum is used for determining moisture (these devices are designated as infrared devices hereinbelow). Additionally, devices are known which operate in the microwave range; however, these devices will not be further examined herein.

All spectroscopic determinations of concentration proceed from the so-called Beer's law which for parallel beam paths reads:

$$I_\lambda = I_{\lambda}\cdot\exp(-K_\lambda X) \quad (1)$$

where, with respect to a set wavelength $\lambda$, the value $I_\lambda$ indicates the beamed intensity, the value $I_\lambda$ indicates the intensity of the beam after passing the absorption distance having a length X, and the value $K_\lambda$ indicates the absorption coefficient.

In the infrared range of the spectrum, the absorption spectrum of water vapor consists of a plurality of single lines, so-called bands, which no longer can be distinguished by customary infrared hygrometers. In place of the various absorption coefficients $K_\lambda$ which apply for the individual lines, an empirical formula applies instead of equation (1), which is mathematically awkward to handle and therefore approximation equations are often used.

Therefore the association of moisture values to the measured intensities is performed by corresponding calibration methods, in which the properties of the devices, such as filter transparency, amplification, detector sensitivity, etc., as well as the pressure dependence, must also be considered.

The spectroscopically operating hygrometers can be assigned to various groups. The most simple in principle are the so-called single beam devices (single beam hygrometers), such as described, e.g. by Hyson, Hicks in J.Appl.Met. 14, 1975, pp. 301 to 307. The customary L$\alpha$ devices also operate as single beam devices. In connection with these single beam devices constant operating conditions must be strictly maintained in order to obtain truly comparable values. In spite of this, frequent test calibrations are necessary to measure changes extending over long periods of time.

It is possible to achieve better accuracy with so-called double beam devices (double beam hygrometers), such as described by Bogomovola et al in Izv. Atm. and Oceanic Phys., vol. 10, 1974, pp. 933 to 942. Comparative measurements are taken with these double beam devices, in particular in a wave range in which the water vapor is absorbed very little or not at all. By developing a quotient it is possible in this way to compensate to a large degree for slow changes in the device.

Often a chopper is introduced into the beam path in spectroscopically operating hygrometers. By the use of this, alternating voltage is obtained for use as signal voltage. This facilitates amplification and filtering. In double beam devices either two separate detectors can be used which, however, must be operated under exactly the same constant conditions, or it is also possible to operate with only one detector by, e.g., alternatingly introducing two filters into the beam path or by modulating (chopping) the two beams with different frequencies.

For physically technical reasons it is not possible to operate with two beams of different wavelength in L$\alpha$ devices. Therefore it has been suggested, e.g. by Buck in Bull.Am.Met.Soc, vol. 57, 1976, pp. 1113 to 1118, to change the absorption distance X. Because L$\alpha$ devices in general have a very short absorption distance, small changes of the value X (see Equation (1)) are very effective. However, a very high degree of accuracy in adjustment is required in this case. A further device for the measurement of water vapor density and of a saturation ratio is known from U.S. Pat. No. 4,394,575.

In spite of the development of a quotient, certain influences which lead to errors in measurements cannot be eliminated in hygrometers operating with two wavelengths. This is the case, for example, if the distribution of spectral intensity of a beam source or the distribution of spectral sensitivity of a detector changes in dependence on the wavelength. For these reasons corrections can only be made by means of calibration tests made at certain time intervals.

However, it is possible that an adsorption layer or even a coating forms on the surfaces of windows, lenses or mirrors, which, because they have an absorption depending on the wavelength, result in false measurement values. Latest measurements under special laboratory conditions have indicated that at dew point temperatures around $-40°$ C. it is possible to get a consistent error of almost $10°$ C. in the determination of the dew point, which error is due to adsorption. It has been suggested to heat the windows, lenses or mirrors to avoid coatings, but this also does not assure that an adsorption layer is reliably avoided.

SUMMARY OF THE INVENTION

It is therefore an object of the invention to exclude, from the beginning, measurement errors primarily based on adsorption effects in infrared hygrometers. In accordance with the present invention, this is attained in a spectroscopically operating infrared hygrometer having a beam source and a detector, in front of each of which a lens arrangement is disposed for focusing and directing the beams. The object of the present invention is achieved in that the beams emitted by the beam source and formed by the lens arrangement disposed in front thereof, are reflected via two pairs of rotating mirrors, fixed in two parallel planes which are at a distance (d) from each other, and via a fixed mirror, disposed in the area of the beam source and the detector, to the lens arrangement placed in front of the detector and are then directed by it to the detector. This creates a succession of short signal pulses in which the amplitudes of the harmonic waves are also evaluated and blanked out during the pauses in order to improve the signal to noise ratio.

An advantageous addition of the invention is the provision of two pairs of rotating mirrors each disposed at the ends of supports, oriented towards the common fixed mirror. Supports are disposed at the set distance (d) in planes which are parallel to each other. The two supports are each fixed on a shaft of a common drive motor in the center between the respective pair of mirrors. The supports for the two pairs of mirrors are radially displaced 90° with respect to said shaft as shown in the drawing.

Two different absorption path lengths are used in the infrared hygrometer according to the invention to eliminate the measurement errors caused by the adsorption effects. Although this concept has already been suggested in connection with Lα devices, it is not possible to simply transfer it to infrared hygrometers. Because the infrared hygrometers, in general operate with considerably longer absorption distances than the Lα devices, an effective and, in practice, easily attainable path length change is attained only by means of the infrared hygrometer of the invention.

It is furthermore possible with the infrared hygrometer of the invention to very rapidly change the absorption distance, so that, by means of the hygrometer of the invention it is possible during measurements over longer periods of time with small time constants, for example, during measurements taken from an airplane, to relate continuously the individual measurement values for the two absorption distances. This constitutes an additional advantage over the Lα devices, because with the infrared hygrometer according to the invention the intermediate calibration no longer is required, which must also be performed from time to time in connection with the Lα devices. The intermediate calibration required in the conventional Lα devices has further disadvantage that it is only later possible to determine, whether the calibration curve has changed, for which reason an exact evaluation of the measurements taken is no longer possible.

In accordance with a preferred embodiment, in a spectroscopically operating infrared hygrometer, the beams emitted by a beam source and formed by a lens arrangement disposed in front thereof, are reflected via two pairs of rotating mirrors, fixed in two parallel planes which are at a fixed distance from each other, and via a fixed mirror, disposed in the area of the beam source and the detector, to the lens arrangement placed in front of the detector and are then directed by it to the detector.

In accordance with a further preferred embodiment of the invention the two pairs of rotating mirrors are each disposed at the ends of supports, the mirrors each being oriented towards the common fixed mirror. The supports holding the pairs of mirrors are disposed at a set distance in planes which are parallel to each other, and the supports are offset by 90° in these planes. Furthermore, the two supports are disposed on a shaft of a common drive motor each in the center between the respective pair of mirrors.

By means of the invention, a simple design of an infrared hygrometer has been achieved, in which a continuous recalibration of the hygrometer takes place by means of the individual measurements changing in rapid succession during absorption distances of different lengths and the subsequent quotient formation of the measurement values. This, in turn, has the advantage that no great demands have to be made on the constancy of the operational values of the beam source or of the detector. Furthermore, since only one wavelength is used with the infrared hygrometer of the invention, changes of the distribution of the spectral intensity of the beam source or of the distribution of the spectral sensitivity of the detector used do not make any difference.

Still other objects, features and attendant advantages of the present invention will become apparent to those skilled in the art from a reading of the following detailed description of the embodiments constructed in accordance therewith, taken in conjunction with the accompanying drawings.

BRIEF DESCRIPTION OF THE DRAWING

The invention of the present application will now be described in more detail with reference to the preferred embodiments of the device, given only by way of example, and with reference to the accompanying drawings, in which:

The drawing illustrates a schematic view of an infrared hygrometer according to the present invention.

DETAILED DESCRIPTION OF A PREFERRED EMBODIMENT

The beam from a beam source ST is arranged in parallel by a lens arrangement L1 and arrives at a second lens arrangement L2 disposed in front of a detector D after being reflected off three mirrors SP2, SP1 and SP3 or SP4, SP1 and SP5. Of the three mirrors used, the mirror SP1 is fixed, while the two pairs of mirrors SP2 and SP3 o: SP4 and SP5 are alternatingly turned into the beam path in order to obtain by this action differing absorption distances.

For this purpose the two pairs of mirrors SP2, SP3 and SP4, SP5 are each disposed at the ends of a support T1 or T2 which is supported a substantially center position of the support. The supports T1 and T2 are fixed on a shaft A driven by a motor M at a distance d from one another in parallel planes, i.e. parallel to each other but turned by 90° in respect to each other.

In the schematic view the disposition of the supports T1 and T2, offset by 90° from each other, is made apparent by the drawing of the support T2 with dashed lines. It is to be indicated by means of these dashed lines that the support T2 has been turned by 90° in respect to the support T1, i.e. it extends vertically out of the plane of the drawing.

Because the two pairs of mirrors SP2, SP3 and SP4, SP5 are each in a fixed position for only a short time because of the rotation of the supports T1 and T2, short signal pulses with intermediate pauses are generated at the output of the detector D.

During these pauses the detector only emits noise. To improve the signal to noise ratio, the signal is therefore blanked out during the pauses. Furthermore, the harmonic waves of the signal pulse sequence, which slowly decrease in amplitude during very short pulses, are also filtered out and evaluated to improve the signal to noise ratio, such as described, for example, in German Patent No. 19 45 087.

Although in the arrangement according to the invention the same optical elements are not exclusively used during individual measurements with different absorption distances, because two pairs of mirrors SP2, SP3 and SP4, SP5 are brought into the beam path, this is not a disadvantage. With mirrors of identical construction and design it is always possible to assume that the adsorption and coating layers are also identical.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. In an apparatus for calibrating a spectroscopically operating infrared hygrometer having a beam source, a detector, a lens arrangement disposed in front of the beam source and the detector for focusing beams generated by the beam source, the improvement comprising: pairs of rotating mirrors being fixed in two parallel planes which are at a fixed distance (d) from each other, a common fixed mirror, for reflecting the beams to the lens arrangement placed in front of the detector, wherein the beams are directed by the fixed mirror to the detector, and wherein a succession of short signal pulses in which amplitudes of harmonic waves are also evaluated and blanked out during the pauses in order to improve the signal to noise ratio is obtained.

2. In an apparatus for calibrating an infrared hygrometer in accordance with claim 1, further comprising two supports for supporting said pairs of rotating mirrors are each disposed at ends thereof, said rotating mirrors being oriented towards the common fixed mirror, said supports being disposed at a set distance d from one another and in planes which are parallel to each other, said mirror pairs being offset by 90° from each other, and said two supports are each fixed on a shaft of a common drive motor disposed in a substantial center portion of said supports between the respective pair of mirrors.

* * * * *